(12) United States Patent
Yoshii et al.

(10) Patent No.: US 8,778,839 B2
(45) Date of Patent: Jul. 15, 2014

(54) HERBICIDAL COMPOSITION

(75) Inventors: Hiroshi Yoshii, Kusatsu (JP); Ryu Yamada, Kusatsu (JP)

(73) Assignee: Ishihara Sangyo Kaisha, Ltd., Osaka-shi (JP)

( * ) Notice: Subject to any disclaimer, the term of this patent is extended or adjusted under 35 U.S.C. 154(b) by 979 days.

(21) Appl. No.: 12/280,567

(22) PCT Filed: Mar. 13, 2007

(86) PCT No.: PCT/JP2007/055580
§ 371 (c)(1),
(2), (4) Date: Aug. 25, 2008

(87) PCT Pub. No.: WO2007/119435
PCT Pub. Date: Oct. 25, 2007

(65) Prior Publication Data
US 2009/0170702 A1    Jul. 2, 2009

(30) Foreign Application Priority Data

Mar. 24, 2006   (JP) ................. 2006-083322

(51) Int. Cl.
*A01N 43/46* (2006.01)
*A01N 43/54* (2006.01)
*A01N 43/66* (2006.01)

(52) U.S. Cl.
USPC ........... 504/227; 504/230; 504/239; 504/242; 504/243

(58) Field of Classification Search
CPC .............................. A01N 43/54; A01N 43/66
USPC ....................................... 504/127
See application file for complete search history.

(56) References Cited

U.S. PATENT DOCUMENTS

| 6,664,213 B1 | 12/2003 | Furusawa et al. |
| 2002/0091066 A1 | 7/2002 | Wurtz et al. |
| 2003/0100449 A1 | 5/2003 | Maeda et al. |
| 2006/0154824 A1 | 7/2006 | Yoshii et al. |
| 2007/0066486 A1 | 3/2007 | Kawanaka et al. |

FOREIGN PATENT DOCUMENTS

| EP | 0 598 515 A1 | 5/1994 |
| EP | 0 968 649 | 1/2000 |
| EP | 1 277 405 | 1/2003 |
| EP | 1 586 238 | 10/2005 |
| EP | 1 741 339 | 1/2007 |
| JP | 2000-159603 | 6/2000 |
| JP | 2001-122702 | 5/2001 |
| JP | 2006-241041 | 9/2006 |
| JP | 2009-509949 | 3/2009 |
| WO | 01 13724 | 3/2001 |
| WO | 01 97615 | 12/2001 |
| WO | 2004 023876 | 3/2004 |
| WO | WO 2005/092104 A1 | 6/2005 |
| WO | 2007 036585 | 4/2007 |

OTHER PUBLICATIONS

U.S. Appl. No. 13/049,169, filed Mar. 16, 2011, Yoshii, et al.
Office action issued Jul. 31, 2012 in Patent Application No. 2007-059486 with English language translation.
U.S. Appl. No. 11/908,521, filed Sep. 13, 2007, Yoshii, et al.
Green J.M. et al., "Enhancing the Biological Activity of Nicosulfuron with Ph Adjusters", Weed Technology, vol. 17, No. 2, pp. 338-345, XP008041926, (2003).

*Primary Examiner* — Alton Pryor
(74) *Attorney, Agent, or Firm* — Oblon, Spivak, McClelland, Maier & Neustadt, L.L.P.

(57) ABSTRACT

Improvement of the effect of a herbicidally active ingredient and reduction of its dosage are required so as to reduce the environment load on a site where the herbicide is applied or the periphery thereof, more than ever. A herbicidal composition comprising (1) a herbicidal sulfonylurea compound or its salt and (2) a polyoxyalkylene alkyl ether phosphate or its salt. A method for controlling undesired plants or inhibiting their growth, by applying such a herbicidal composition.

14 Claims, No Drawings

HERBICIDAL COMPOSITION

CROSS-REFERENCE TO RELATED APPLICATIONS

This application is a 371 of PCT/JP07/55580 filed Mar. 13, 2007 and claims the benefit of JP 2006/083322 filed Mar. 24, 2006.

TECHNICAL FIELD

The present invention relates to a herbicidal composition which improves the herbicidal effect of a herbicidal sulfonylurea compound or its salt by use of a polyoxyalkylene alkyl ether phosphate or its salt.

BACKGROUND ART

Heretofore, in cultivation of crop plants in cropland, it has been desired to control weeds which inhibit the growth or the harvest of crop plants. Further, in non-cropland also, it is beneficial for utilization of the non-cropland to effectively control weeds. Thus, control of weeds is necessary in each of cropland and non-cropland, and various herbicides have been used. However, in recent years, there is a movement to reduce the dosage of a herbicidally active ingredient as far as possible, so as to reduce the environment load at a site where the herbicide is applied or the periphery thereof.

For example, blending of a nonionic surfactant with a spray solution is known to improve the herbicidal effect and to reduce the dosage of the herbicide, and an alkylaryl polyglycol ether type surfactant (tradename: Citowett, manufactured by BASF France) may be mentioned as a general purpose product. Further, EP0598515 discloses remarkable improvement of the herbicidal effect by blending of an ethoxylated fatty amine type surfactant with a vegetable oil and/or a mineral oil in application of nicosulfuron or primisulfuron as a specific herbicidal sulfonylurea compound.
Patent Document 1: EP0598515

DISCLOSURE OF THE INVENTION

Object to be Accomplished by the Invention

It has been desired to improve the effect of a herbicidally active ingredient and to reduce the dosage as far as possible, so as to reduce the environment load on a site where the herbicide is applied or the periphery thereof more than ever.

Means to Accomplish the Object

The present inventors have conducted extensive studies to accomplish the above object and as a result, found that the herbicidal effect of a herbicidal sulfonylurea compound or its salt can be remarkably improved by use of a specific compound, and accomplished the present invention.

Namely, the present invention relates to a herbicidal composition comprising (1) a herbicidal sulfonylurea compound or its salt and (2) a polyoxyalkylene alkyl ether phosphate or its salt. The present invention further relates to a method for controlling undesired plants or inhibiting their growth, which comprises applying (1) a herbicidal sulfonylurea compound or its salt and (2) a polyoxyalkylene alkyl ether phosphate or its salt, to the undesired plants or to a place where they grow. Still further, the present invention relates to a method for improving the herbicidal effect of (1) a herbicidal sulfonylurea compound or its salt, by using (2) a polyoxyalkylene alkyl ether phosphate or its salt.

Effects of the Invention

According to the present invention, the herbicidal effect of a herbicidal sulfonylurea compound (hereinafter referred to as a SU compound) or its salt is effectively brought about and improved by a polyoxyalkylene alkyl ether phosphate (hereinafter referred to as a POA alkyl ether phosphate) or its salt. Further, the dosage of the herbicide can be reduced by the POA alkyl ether phosphate or its salt, whereby the environment load on a site where the herbicide is applied or the periphery thereof can be remarkably reduced and further, the reduction in the dosage of the herbicide contributes to remarkable reduction in the cost required for storage or transportation.

BEST MODE FOR CARRYING OUT THE INVENTION

The herbicidal composition of the present invention comprises a SU compound or its salt and a POA alkyl ether phosphate or its salt. For example, the present invention is applied in such a manner that (1) a SU compound or its salt is formulated by using various additives, the formulation is diluted with e.g. water together with a POA alkyl ether phosphate or its salt, and the diluted liquid is applied to undesired plants or to a place where they grow, or (2) a SU compound or its salt, and a POA alkyl ether phosphate or its salt, are formulated together with various additives, and the resulting formulation diluted with e.g. water or as it is without dilution, is applied to undesired plants or to a place where they grow.

The SU compound in the present invention is a compound having a partial structure of the following formula (I):

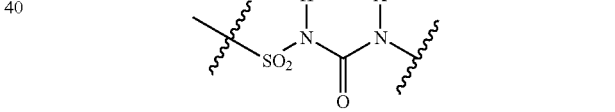

wherein X is a hydrogen atom or an alkyl group, and may be amidosulfuron, azimsulfuron, bensulfuron-methyl, chlorimuron-ethyl, chlorsulfuron, cinosulfuron, cyclosulfamuron, ethametsulfuron-methyl, ethoxysulfuron, flazasulfuron, flucetosulfuron, flupyrsulfuron, foramsulfuron, halosulfuron-methyl, imazosulfuron, iodosulfuron-methyl, mesosulfuron-methyl, metsulfuron-methyl, nicosulfuron, orthosulfamuron, oxasulfuron, primisulfuron-methyl, prosulfuron, pyrazosulfuron-ethyl, rimsulfuron, sulfometuron-methyl, sulfosulfuron, thifensulfuron-methyl, triasulfuron, tribenuron-methyl, trifloxysulfuron, triflusulfuron-methyl, tritosulfuron, TH-547 by developing code, or a compound disclosed in WO2005092104.

As the salt of the SU compound in the present invention, various salts may be mentioned, such as a salt with an alkali metal such as sodium or potassium, a salt with an alkylene earth metal such as magnesium or calcium, and a salt with an amine such as monomethylamine, dimethylamine or triethylamine.

Among them, preferred is flazasulfuron, foramsulfuron, halosulfuron-methyl, iodosulfuron-methyl-sodium, nicosulfuron, prosulfuron, rimsulfuron, trifloxysulfuron-sodium, tritosulfuron or the like, and among them, particularly preferred is flazasulfuron, foramsulfuron, nicosulfuron or the like.

The POA alkyl ether phosphate in the present invention may, for example, be a mono-POA alkyl ether phosphate, a di-POA alkyl ether phosphate or a tri-POA alkyl ether phosphate, having 1 to 3 POA alkyl ether moieties bonded to a phosphorus atom, and in a case where a plurality of POA alkyl ether moieties are bonded to a phosphorus atom, they may be the same or the different. In the present invention, the above-described phosphates may optionally be mixed.

The alkyl moiety in the POA alkyl ether phosphate in the present invention may be either linear or blanched, and it preferably has, for example, from about 8 to about 20 carbon atoms. Specific examples thereof include octyl, nonyl, decyl, undecyl, dodecyl, tridecyl, tetradecyl, pentadecyl, hexadecyl, heptadecyl, octadecyl, nonadecyl and eicosyl.

In the present invention, the number of addition of POA moiety in the POA alkyl ether phosphate is from about 1 to about 50, preferably from about 1 to about 20. Further, the alkylene oxide moiety in the POA alkyl ether phosphate may be linear or branched, and it preferably has, for example, from about 2 to about 3 carbon atoms. Specific examples thereof include ethylene oxide, propylene oxide and —CH(CH$_3$)CH$_2$O—. Their copolymers and block copolymers may also be mentioned. The position of substitution of the alkylene oxide moiety is not particularly limited.

In the present invention, as the salt of the POA alkyl ether phosphate, various salts may be mentioned, such as a salt with an alkali metal such as sodium or potassium; a salt with an alkaline earth metal such as magnesium or calcium; a salt with NH$_4^+$; and an amine salt such as a salt with a monoethanolamine, a salt with a diethanolamine, a salt with a triethanolamine, a salt with a trimethylamine, a salt with a triethylamine, a salt with a tributylamine, a salt with a diisopropylethylamine or a salt with morpholine.

In the present invention, in a case where the POA alkyl ether phosphate is used in the form of a salt, the POA alkyl ether phosphate may be added to a spray solution or a formulation, followed by neutralization with a base to form a salt in a spray tank or during formulation. Otherwise, the POA alkyl ether phosphate as it is or in a solution state such as an aqueous solution, is preliminarily neutralized with a base to form a salt, which is then added to a spray solution or a formulation. In either case, the base to be used may be added as it is or in a solution state such as an aqueous solution.

The base to be used for the neutralization may be either an inorganic base or an organic base. The inorganic base may, for example, be an alkali metal carbonate such as sodium carbonate or potassium carbonate; an alkali metal hydrogencarbonate such as sodium hydrogencarbonate or potassium hydrogencarbonate; an alkaline earth metal carbonate such as magnesium carbonate, calcium carbonate or barium carbonate; an alkali metal hydroxide such as lithium hydroxide, sodium hydroxide or potassium hydroxide; or an alkaline earth metal hydroxide such as magnesium hydroxide, calcium hydroxide or barium hydroxide. The organic base may, for example, be an amine such as ammonia, monoethanolamine, diethanolamine, triethanolamine, trimethylamine, triethylamine, tributylamine, diisopropylethylamine or morpholine. The base may be used alone or as a mixture of two or more of them.

As examples of the chemical structure of the POA alkyl ether phosphate in the present invention, compounds of the following formulae (II), (III) and (IV) may be mentioned. However, the present invention is by no means restricted thereto.

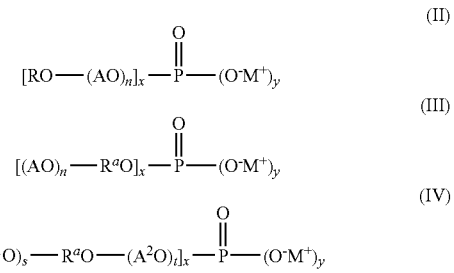

In the above formulae, R is an alkyl, each of $R^a$, A, $A^1$ and $A^2$ is an alkylene, $M^+$ is a hydrogen ion, a metal ion, ammonium or an organic ammonium, each of n, s and t is an integer of at least 1, and x and y satisfy x+y=3, x is an integer of 1, 2 or 3 and y is an integer of 0, 1 or 2. When x is at least 2, R's, $R^a$'s, A's, $A^1$'s, $A^2$'s and n's in the respective [RO(AO)$_n$], [(AO)$_n$R$^a$O] and [(A$^1$O)$_s$R$^a$O(A$^2$O)$_t$] may be the same or different. When y is 2, $M^+$ may be the same or different. In the formula (IV), $A^1$ and $A^2$ may be the same or different.

The POA alkyl ether phosphate or its salt in the present invention is also known, for example, as a phosphate ester of an alkoxylated alcohol or its salt, a phosphated alcohol alkoxylate or its salt, or a (polyoxyalkylene alcohol) phosphate or its salt. They are all included in the POA alkyl ether phosphate or its salt used in the present invention, and the present invention is not limited thereto.

In the present invention, a surfactant containing a POA alkyl ether phosphate or its salt may be used, and the following may be mentioned as specific examples thereof.

NIKKOL DLP-10, NIKKOL DOP-8NV, NIKKOL DDP-2, NIKKOL DDP-4, NIKKOL DDP-6, NIKKOL DDP-8, NIKKOL DDP-10, NIKKOL TLP-4, NIKKOL TCP-5, NIKKOL TDP-2, NIKKOL TDP-6, NIKKOL TDP-8, NIKKOL TDP-10, etc., tradenames, manufactured by NIKKO CHEMICALS CO., LTD.

PLYSURF A212C, PLYSURF A215C, PLYSURF A208B, PLYSURF A219B, etc., tradenames, manufactured by DAI-ICHI KOGYO SEIYAKU CO., LTD.

PHOSPHANOL ED-200, PHOSPHANOL RA-600, PHOSPHANOL ML-220, PHOSPHANOL ML-240, PHOSPHANOL RD-510Y, PHOSPHANOL RS-410, PHOSPHANOL RS-610, PHOSPHANOL RS-710, PHOSPHANOL RL-210, PHOSPHANOL RL-310, PHOSPHANOL RB-410, PHOSPHANOL RS-610NA, PHOSPHANOL SC-6103, PHOSPHANOL RS-710M, PHOSPHANOL GB-520, PHOSPHANOL RD-720, etc., tradenames, manufactured by TOHO Chemical Industry Co., Ltd.

ADEKA COL PS-440E, ADEKA COL PS-509E, ADEKA COL PS-807, ADEKA COL PS-810, ADEKA COL PS-984, etc., tradenames, manufactured by ADEKA CORPORATION.

PHOSPHOLAN 5AP, PHOSPHOLAN PS-131, PHOSPHOLAN PS-220, PHOSPHOLAN PS-222, PHOSPHOLAN PS-236, PHOSPHOLAN PS-331, PHOSPHOLAN PS-810, PHOSPHOLAN PS-900, etc., tradenames, manufactured by AKZO NOVEL.

In the present invention, a salt as a coadjuvant may be used if required, in order to more significantly improve the herbicidal effect of the SU compound or its salt, to expand the range of weeds to be controlled against which the herbicidal effect is exhibited, or to expand the timing for the application of the herbicide. Such a salt may be either an inorganic salt or an organic salt. The inorganic salt may, for example, be a phosphate such as Na$_2$HPO$_4$, NaH$_2$PO$_4$, K$_2$HPO$_4$ or KH$_2$PO$_4$. The organic salt may, for example, be an aliphatic carboxylate such as a citrate, a succinate, a malate, an oxalate, a lactate, a gluconate or a heptonate, an aminopolycarboxylate such as a salt of ethylenediaminetetraacetic acid (EDTA), a salt of iminodiacetic acid (IDA), a salt of nitrilotriacetic acid (NTA), a salt of ethylene glycol bis(2-aminoethyl ether)-N, N,N',N'-tetraacetic acid (EGTA), a salt of ethylenetriaminepentaacetic acid (DTPA), or a salt of cyclohexanediaminetetraacetic acid (CDTA), an amino acid salt, a hydroxycarboxylate or an aromatic carboxylate. Among them, the inorganic salt is preferably a phosphate. The organic salt is preferably a citrate, an oxalate, a succinate, an EDTA salt or an amino acid salt. The amino acid salt is more preferably glutamate. The salt is preferably a sodium salt.

The herbicidal composition of the present invention may be either in a form such that the herbicidal composition containing the SU compound or its salt, and the POA alkyl ether phosphate or its salt, or a surfactant containing it, are mixed, for example, at the time of application, or in a form such that they are preliminarily formulated. The same applies to a case where a salt as a coadjuvant is used. Various additives may be used if desired, when the SU compound or its salt and the POA alkyl ether phosphate or its salt are formulated, or when a salt as a coadjuvant is further added to the above compounds and formulated. The additives to be used are not particularly limited so long as they can be used in this technical field, and examples thereof include another surfactant (a surfactant other than a surfactant containing the POA alkyl ether phosphate or its salt), a carrier, a binder, a vegetable oil, a mineral oil, an anti-settling agent, a thickener, an antifoaming agent and an antifreezing agent. Formulation may be carried out in accordance with a conventional method in this technical field.

In the present invention, a herbicidal compound other than the SU compound or its salt may be mixed or used in combination if desired, whereby more excellent effects or activity is exhibited in some cases. For example, it may sometimes be possible to improve e.g. the range of the weeds to be controlled, the timing for the application of the herbicide or the herbicidal activities. The SU compound or its salt and another herbicidal compound may be individually prepared and mixed at the time of application, or they may be formulated together and applied. Such another herbicidal compound may suitably be selected from the following compound groups (1) to (11) (common names including ones under application for approval by ISO). Even when not specifically mentioned here, in a case where such compounds have salts, alkyl esters, structural isomers such as optical isomers etc., they are, of course, all included.

(1) Those which are believed to exhibit herbicidal effects by disturbing hormone activities of plants, such as a phenoxy type such as 2,4-D, 2,4-DB, 2,4-DP, MCPA, MCPB, MCPP, naproanilide or clomeprop, an aromatic carboxylic acid type such as 2,3,6-TBA, dicamba, dichlobenil, picloram, triclopyr, clopyralid or aminopyralid, and others such as naptalam, benazolin, quinclorac, quinmerac, diflufenzopyr and thiazopyr.

(2) Those which are believed to exhibit herbicidal effects by inhibiting photosynthesis of plants, such as a urea type such as chlorotoluron, diuron, fluometuron, linuron, isoproturon, metobenzuron or tebuthiuron, a triazine type such as simazine, atrazine, atratone, simetryn, prometryn, dimethametryn, hexazinone, metribuzin, terbuthylazine, cyanazine, ametryn, cybutryne, triaziflam or propazine, a uracil type such as bromacil, lenacil or terbacil, an anilide type such as propanil or cypromid, a carbamate type such as swep, desmedipham or phenmedipham, a hydroxybenzonitrile type such as bromoxynil, bromoxynil-octanoate or ioxynil, and others such as pyridate, bentazone, amicarbazone and methazole.

(3) Quaternary ammonium salt type such as paraquat or diquat, which is believed to be converted to free radicals by itself to form active oxygen in the plant body.

(4) Those which are believed to exhibit herbicidal effects by inhibiting chlorophyll biosynthesis of plants and abnormally accumulating a photosensitizing peroxide substance in the plant body, such as a diphenylether type such as nitrofen, chlomethoxyfen, bifenox, acifluorfen-sodium, fomesafen, oxyfluorfen, lactofen or ethoxyfen-ethyl, a cyclic imide type such as chlorphthalim, flumioxazin, flumiclorac-pentyl or fluthiacet-methyl, and others such as oxadiargyl, oxadiazon, sulfentrazone, carfentrazone-ethyl, thidiazimin, pentoxazone, azafenidin, isopropazole, pyraflufen-ethyl, benzfendizone, butafenacil, metobenzuron, cinidon-ethyl, flupoxam, fluazolate, profluazol, pyrachlonil, flufenpyr-ethyl and bencarbazone.

(5) Those which are believed to exhibit herbicidal effects characterized by bleaching activities by inhibiting chromogenesis of plants such as carotenoids, such as a pyridazinone type such as norflurazon, chloridazon or metflurazon, a pyrazole type such as pyrazolate, pyrazoxyfen, benzofenap, topramezone (BAS-670H) or pyrasulfotole, and others such as amitrol, fluridone, flurtamone, diflufenican, methoxyphenone, clomazone, sulcotrione, mesotrione, tembotrione, tefuryltrione (AVH-301), isoxaflutole, difenzoquat, isoxachlortole, benzobicyclon, picolinafen and beflubutamid.

(6) Those which exhibit strong herbicidal effects specifically to gramineous plants, such as an aryloxyphenoxypropionic acid type such as diclofop-methyl, flamprop-M-methyl, pyriphenop-sodium, fluazifop-butyl, haloxyfop-methyl, quizalofop-ethyl, cyhalofop-butyl, fenoxaprop-ethyl or metamifop-propyl, and a cyclohexanedione type such as alloxydim-sodium, clethodim, sethoxydim, tralkoxydim, butroxydim, tepraloxydim, caloxydim, clefoxydim or profoxydim.

(7) Those which are believed to exhibit herbicidal effects by inhibiting an amino acid biosynthesis of plants, such as a sulfonylurea type such as amidosulfuron, azimsulfuron, bensulfuron-methyl, chlorimuron-ethyl, chlorsulfuron, cinosulfuron, cyclosulfamuron, ethametsulfuron-methyl, ethoxysulfuron, flazasulfuron, flucetosulfuron, flupyrsulfuron, foramsulfuron, halosulfuron-methyl, imazosulfuron, iodosulfuron-methyl-sodium, mesosulfuron-methyl, metsulfuron-methyl, nicosulfuron, orthosulfamuron, oxasulfuron, primisulfuron-methyl, prosulfuron, pyrazosulfuron-ethyl, rimsulfuron, sulfometuron-methyl, sulfosulfuron, thifensulfuron-methyl, triasulfuron, tribenuron-methyl, trifloxysulfuron-sodium, triflusulfuron-methyl, tritosulfuron, TH-547, or a compound disclosed in WO2005092104, a triazolopyrimidinesulfonamide type such as flumetsulam, metosulam, diclosulam, cloransulam-methyl, florasulam, metosulfam or penoxsulam, an imidazolinone type such as imazapyr, imazethapyr, imazaquin, imazamox, imazamethabenz or imazapic, a pyrimidinylsalicylic acid type such as pyrithiobac-sodium, bispyribac-sodium, pyriminobac-methyl, pyribenzoxim, pyriftalid or pyrimisulfan (KUH-021), a sulfonylaminocarbonyltriazolinone type such as flucarbazone or procarbazone-sodium, and others such as glyphosate, glyphosate-sodium, glyphosate-potassium, glyphosate-ammonium, glyphosate-isopropylamine, sulfosate, glufosinate, glufosinate-ammonium and bilanafos.

(8) Those which are believed to exhibit herbicidal effects by inhibiting cell mitoses of plants, such as a dinitroaniline type such as trifluralin, oryzalin, nitralin, pendimethalin, ethalfluralin, benfluralin or prodiamine, an amide type such as bensulide, napronamide or pronamide, an organic phosphorus type such as amiprofos-methyl, butamifos, anilofos or piperophos, a phenylcarbamate type such as propham, chlorpropham or barban, a cumylamine type such as daimuron, cumyluron or bromobutide, and others such as asulam, dithiopyr and thiazopyr.

(9) Those which are believed to exhibit herbicidal effects by inhibiting protein biosynthesis or lipid biosynthesis of plants, such as a chloroacetamide type such as alachlor, metazachlor, butachlor, pretilachlor, metolachlor, S-metolachlor, thenylchlor, pethoxamid, acetochlor, propachlor or propisochlor, a carbamate type such as molinate, dimepiperate or pyributicarb, and others such as etobenzanid, mefenacet, flufenacet, tridiphane, cafenstrole, fentrazamide, oxaziclomefone, indanofan, dimethenamid, benfuresate and pyroxasulfone (KIH-485).

(10) A thiocarbamate type such as EPTC, butylate, vernolate, pebulate, cycloate, prosulfocarb, esprocarb, thiobencarb, diallate or triallate, and others such as MSMA, DSMA, endothall, ethofumesate, sodium chlorate, pelargonic acid, fosamine, pinoxaden and HOK-201.

(11) Those which are believed to exhibit herbicidal effects by being parasitic on plants, such as *Xanthomonas campestris, Epicoccosurus nematosurus, Exserohilum monoseras* and *Drechsrela monoceras*.

In the present invention, the mix ratio of the SU compound or its salt to the POA alkyl ether phosphate or its salt can not generally be defined since it is suitably changed depending upon the types of the SU compound and the POA alkyl ether phosphate, the types of the formulations, weather conditions, the type or the size of weeds to be controlled, etc. However, the mix ratio is, for example, from 13:1 to 1:10,000, preferably from 6:1 to 1:3,000, more preferably from 3:1 to 1:300, furthermore preferably from 1:1 to 1:30, by weight ratio.

In the present invention, in a case where a salt as a coadjuvant is further used, the ratio of the POA alkyl ether phosphate or its salt to such a salt can not generally be defined since it is suitably changed depending upon the type of the SU compound or its salt, the type of the POA alkyl ether phosphate or its salt, the type of such a salt, the types of the formulations, weather conditions, the type or the size of weeds to be controlled, etc. However, the ratio is, for example, from 500:1 to 1:5, preferably from 50:1 to 1:1, more preferably from 25:1 to 1:1, by weight ratio.

Further, the mix ratios for various applications are as follows for example.

(1) In a case where the SU compound or its salt is formulated by using various additives, the obtained formulation is diluted with e.g. water together with the POA alkyl ether phosphate or its salt, and the diluted liquid is applied to undesired plants or to a place where they grow, the application can be carried out as follows. That is, when the formulated SU compound or its salt and the POA alkyl ether phosphate or its salt are diluted with e.g. water in an amount of from 30 to 5,000 L/ha, preferably from 50 to 2,000 L/ha, the POA alkyl ether phosphate or its salt is added in an amount of from 0.005 to 4 wt %, preferably from 0.01 to 2 wt %, based on the diluted liquid.

(2) In a case where the SU compound or its salt, and the POA alkyl ether phosphate or its salt, are formulated together with various additives, and the obtained formulation diluted with e.g. water or as it is without dilution, is applied to undesired plants or to a place where they grow, the application can be carried out as follows. That is, the SU compound or its salt and the POA alkyl ether phosphate or its salt are blended to be within the above weight ratio, followed by application.

(3) In a case where one or more other herbicidal compounds are mixed with the SU compound or its salt, the application can be carried out in accordance with the blend ratio in the above (1) or (2).

(4) In a case where a salt as a coadjuvant is further used in each of the above cases (1), (2) and (3), the application can be carried out as follows. Namely, at the time of dilution with e.g. water as described above, the salt as a coadjuvant is added in an amount of from 0.0001 to 0.05 wt %, preferably from 0.001 to 0.02 wt %, based on the diluted liquid, followed by application.

The herbicidal composition of the present invention is capable of controlling a wide range of undesired plants such as sedges (or cyperaceae) such as rice flatsedge (*Cyperus iria* L.) or purple nutsedge (*Cyperus rotundus* L.), grasses (or gramineae) such as barnyardgrass (*Echinochloa crus-galli* L.), crabgrass (*Digitaria sanguinalis* L.), greenfoxtail (*Setaria viridis* L.), goosegrass (*Eleusine indica* L.), wild oat (*Avena-fatua* L.), johnsongrass (*Sorghum halepense* L.) or quackgrass (*Agropyron repens* L.), or broad leaves such as velvetleaf (*Abutilon theophrasti* MEDIC.), tall morningglory (*Ipomoea purpurea* L.), common lambsquarters (*Chenopodium album* L.), prickly sida (*Sida spinosa* L.), common purslane (*Portulaca oleracea* L.), redroot pigweed (*Amaranthus retroflexus* L.), sicklepod (*Cassia obtusifolia* L.), black nightshade (*Solanum nigrum* L.), pale smartweed (*Polygonum lapathifolium* L.), common chickweed (*Stellaria media* L.), common cocklebur (*Xanthium strumarium* L.), flexuous bittercress (*Cardamine flexuosa* WITH.), henbit (*Lamium amplexicaule* L.) or threeseeded copperleaf (*Acalypha australis* L.), by application such as foliar application to undesired plants or to a place where they grow. Thus, its application range extends not only to crop plant fields but also to agricultural fields such as orchards and mulberry fields and non-agricultural fields such as forest land, farm roads, play grounds, factory sites and lawn fields.

Some preferred embodiments of the present invention will be described. However, the present invention is by no means limited thereto.

(1) A herbicidal composition comprising a) a herbicidally effective amount of a SU compound or its salt and b) a POA alkyl ether phosphate or its salt in an amount effective to increase the herbicidal activity.

(2) A herbicidal composition comprising a) a herbicidally effective amount of a SU compound or its salt, b) a POA alkyl ether phosphate or its salt in an amount effective to increase the herbicidal activity and c) a salt in an effective amount as a coadjuvant.

(3) A herbicidal composition comprising a SU compound or its salt and a POA alkyl ether phosphate or its salt together with various additives formulated.

(4) A herbicidal composition comprising a SU compound or its salt, a POA alkyl ether phosphate or its salt and a salt as a coadjuvant together with various additives formulated.

(5) A herbicidal composition comprising a herbicidally effective amount of a SU compound or its salt, and a POA alkyl ether phosphate or its salt in an amount effective to increase the herbicidal activity, in a water-diluted liquid state which can be applied to undesired plants or to a place where they grow.

(6) A herbicidal composition comprising a herbicidally effective amount of a SU compound or its salt, a POA alkyl ether phosphate or its salt in an amount effective to increase the herbicidal activity and a salt in an effective amount as a coadjuvant, in a water-diluted liquid state which can be applied to undesired plants or to a place where they grow.

(7) The above herbicidal composition which further contains a herbicidally effective amount of another herbicidal compound.
(8) The above herbicidal composition having the herbicidal effect of the SU compound or its salt improved by the POA alkyl ether phosphate or its salt.
(9) The above herbicidal composition having the herbicidal effect of the SU compound or its salt improved by the POA alkyl ether phosphate or its salt and the salt as a coadjuvant.
(10) The above herbicidal composition having the herbicidal effect of a herbicidal composition comprising a SU compound or its salt and another herbicidal compound improved by the POA alkyl ether phosphate or its salt.
(11) The above herbicidal composition having the herbicidal effect of a herbicidal composition comprising a SU compound or its salt and another herbicidal compound improved by the POA alkyl ether phosphate or its salt and the salt as a coadjuvant.
(12) A method for controlling undesired plants or inhibiting their growth, which comprises applying a) a herbicidally effective amount of a SU compound or its salt and b) a POA alkyl ether phosphate or its salt in an amount effective to increase the herbicidal activity, to is the undesired plants or to a place where they grow.
(13) A method for controlling undesired plants or inhibiting their growth, which comprises applying a) a herbicidally effective amount of a SU compound or its salt, b) a POA alkyl ether phosphate or its salt in an amount effective to increase the herbicidal activity and c) a salt in an effective amount as a coadjuvant, to the undesired plants or to a place where they grow.
(14) A method for controlling undesired plants or inhibiting their growth, which comprises (i) formulating a SU compound or its salt using various additives, (ii) diluting the formulation with water, together with a POA alkyl ether phosphate or its salt in an amount effective to increase the herbicidal activity, and (iii) applying the diluted liquid to the undesired plants or to a place where they grow.
(15) A method for controlling undesired plants or inhibiting their growth, which comprises (i) formulating a SU compound or its salt using various additives, (ii) formulating a POA alkyl ether phosphate or its salt using various additives, (iii) diluting these formulations with water, and (iv) applying the diluted liquid to the undesired plants or to a place where they grow.
(16) A method for controlling undesired plants or inhibiting their growth, which comprises (i) formulating a SU compound or its salt using various additives, (ii) diluting the formulation with water, together with a POA alkyl ether phosphate or its salt in an amount effective to increase the herbicidal activity and a salt in an effective amount as a coadjuvant, and (iii) applying the diluted liquid to the undesired plants or to a place where they grow.
(17) A method for controlling undesired plants or inhibiting their growth, which comprises (i) formulating a SU compound or its salt using various additives, (ii) formulating a POA alkyl ether phosphate or its salt and a salt as a coadjuvant together with various additives, (iii) diluting these formulations with water, and (iv) applying the diluted liquid to the undesired plants or to a place where they grow.
(18) A method for controlling undesired plants or inhibiting their growth, which comprises (i) formulating a SU compound or its salt and a POA alkyl ether phosphate or its salt together with various additives, (ii) diluting the formulation with water, and (iii) applying the diluted liquid to the undesired plants or to a place where they grow.
(19) A method for controlling undesired plants or inhibiting their growth, which comprises (i) formulating a SU compound or its salt and a POA alkyl ether phosphate or its salt together with various additives, (ii) diluting the formulation with water, together with a salt in an effective amount as a coadjuvant, and (iii) applying the diluted liquid to the undesired plants or to a place where they grow.
(20) A method for controlling undesired plants or inhibiting their growth, which comprises (i) formulating a SU compound or its salt and a POA alkyl ether phosphate or its salt together with various additives, (ii) formulating a salt as a coadjuvant using various additives, (iii) diluting these formulations with water, and (iv) applying the diluted liquid to the undesired plants or to a place where they grow.
(21) A method for controlling undesired plants or inhibiting their growth, which comprises (i) formulating a SU compound or its salt, a POA alkyl ether phosphate or its salt and a salt as a coadjuvant together with various additives, (ii) diluting the formulation with water, and (iii) applying the diluted liquid to the undesired plants or to a place where they grow.
(22) A method for controlling undesired plants or inhibiting their growth, which comprises (i) formulating a SU compound or its salt and a salt as a coadjuvant together with various additives, (ii) diluting the formulation with water, together with a POA alkyl ether phosphate or its salt in an amount effective to increase the herbicidal activity, and (iii) applying the diluted liquid to the undesired plants or to a place where they grow.
(23) A method for controlling undesired plants or inhibiting their growth, which comprises (i) formulating a SU compound or its salt and a salt as a coadjuvant together with various additives, (ii) formulating a POA alkyl ether phosphate or its salt using various additives, (iii) diluting these formulations with water, and (iv) applying the diluted liquid to the undesired plants or to a place where they grow.
(24) The above method for controlling undesired plants or inhibiting their growth, by foliar application to the undesired plants.
(25) The above method for controlling undesired plants or inhibiting their growth, wherein a herbicidally effective amount of another herbicidal compound is further applied.
(26) A method for controlling undesired plants or inhibiting their growth, which comprises applying a) a herbicidally effective amount of SU compound or its salt, b) a POA alkyl ether phosphate or its salt in an amount effective to increase the herbicidal activity and c) a herbicidally effective amount of another herbicidal compound, to the undesired plants or to a place where they grow.
(27) A method for controlling undesired plants or inhibiting their growth, which comprises applying a) a herbicidally effective amount of a SU compound or its salt, b) a POA alkyl ether phosphate or its salt in an amount effective to increase the herbicidal activity, c) a salt in an effective amount as a coadjuvant and d) a herbicidally effective amount of another herbicidal compound, to the undesired plants or to a place where they grow.
(28) A method for controlling undesired plants or inhibiting their growth, which comprises (i) formulating a SU compound or its salt and another herbicidal compound together with various additives, (ii) diluting the formulation with water, together with a POA alkyl ether phosphate or its salt in an amount effective to increase the herbicidal activity, and (iii) applying the diluted liquid to the undesired plants or to a place where they grow.
(29) A method for controlling undesired plants or inhibiting their growth, which comprises (i) formulating a SU compound or its salt and another herbicidal compound together with various additives, (ii) formulating a POA alkyl ether phosphate or its salt using various additives, (iii) diluting these formulations with water, and (iv) applying the diluted liquid to the undesired plants or to a place where they grow.

(30) A method for controlling undesired plants or inhibiting their growth, which comprises (i) formulating a SU compound or its salt and another herbicidal compound together with various additives, (ii) diluting the formulation with water, together with a POA alkyl ether phosphate or its salt in an amount effective to increase the herbicidal activity and a salt in an effective amount as a coadjuvant, and (iii) applying the diluted liquid to the undesired plants or to a place where they grow.

(31) A method for controlling undesired plants or inhibiting their growth, which comprises (i) formulating a SU compound or its salt and another herbicidal compound together with various additives, (ii) formulating a POA alkyl ether phosphate or its salt and a salt as a coadjuvant together with various additives, (iii) diluting these formulations with water, and (iv) applying the diluted liquid to the undesired plants or to a place where they grow.

(32) A method for controlling undesired plants or inhibiting their growth, which comprises (i) formulating a SU compound or its salt, another herbicidal compound and a POA alkyl ether phosphate or its salt together with various additives, (ii) diluting the formulation with water, and (iii) applying the diluted liquid to the undesired plants or to a place where they grow.

(33) A method for controlling undesired plants or inhibiting their growth, which comprises (i) formulating a SU compound or its salt, another herbicidal compound and a POA alkyl ether phosphate or its salt together with various additives, (ii) diluting the formulation with water, together with a salt in an effective amount as a coadjuvant, and (iii) applying the diluted liquid to the undesired plants or to a place where they grow.

(34) A method for controlling undesired plants or inhibiting their growth, which comprises (i) formulating a SU compound or its salt, another herbicidal compound and a POA alkyl ether phosphate or its salt together with various additives, (ii) formulating a salt as a coadjuvant using various additives, (iii) diluting these formulations with water, and (iv) applying the diluted liquid to the undesired plants or to a place where they grow.

(35) A method for controlling undesired plants or inhibiting their growth which comprises (i) formulating a SU compound or its salt, another herbicidal compound, a POA alkyl ether phosphate or its salt and a salt as a coadjuvant together with various additives, (ii) diluting the formulation with water, and (iii) applying the diluted liquid to the undesired plants or to a place where they grow.

(36) A method for controlling undesired plants or inhibiting their growth, which comprises (i) formulating a SU compound or its salt, another herbicidal compound and a salt as a coadjuvant together with various additives, (ii) diluting the formulation with water, together with a POA alkyl ether phosphate or its salt in an amount effective to increase the herbicidal activity, and (iii) applying the diluted liquid to the undesired plants or to a place where they grow.

(37) A method for controlling undesired plants or inhibiting their growth, which comprises (i) formulating a SU compound or its salt, another herbicidal compound and a salt as a coadjuvant together with various additives, (ii) formulating a POA alkyl ether phosphate or its salt using various additives, (iii) diluting these formulations with water, and (iv) applying the diluted liquid to the undesired plants or to a place where they grow.

(38) A method for controlling undesired plants or inhibiting their growth, which comprises (i) formulating a SU compound or its salt using various additives, (ii) formulating another herbicidal compound using various additives, (iii) diluting these formulations with water, together with a POA alkyl ether phosphate or its salt in an amount effective to increase the herbicidal activity, and (iv) applying the diluted liquid to the undesired plants or to a place where they grow.

(39) A method for controlling undesired plants or inhibiting their growth, which comprises (i) formulating a SU compound or its salt using various additives, (ii) formulating another herbicidal compound using various additives, (iii) diluting these formulations with water, together with a POA alkyl ether phosphate or its salt in an amount effective to increase the herbicidal activity and a salt in an effective amount as a coadjuvant, and (iv) applying the diluted liquid to the undesired plants or to a place where they grow.

(40) A method for improving the herbicidal effect of a SU compound or its salt, by using a POA alkyl ether phosphate or its salt in an amount effective to increase the herbicidal activity.

(41) A method for improving the herbicidal effect of a SU compound or its salt, by using a POA alkyl ether phosphate or its salt in an amount effective to increase the herbicidal activity and a salt in an effective amount as a coadjuvant.

(42) A method for improving the herbicidal effect of a herbicidal composition comprising a SU compound or its salt and another herbicidal compound, by using a POA alkyl ether phosphate or its salt in an amount effective to increase the herbicidal activity.

(43) A method for improving the herbicidal effect of a herbicidal composition comprising a SU compound or its salt and another herbicidal compound, by using a POA alkyl ether phosphate or its salt in an amount effective to increase the herbicidal activity and a salt in an effective amount as a coadjuvant.

EXAMPLES

Now, the present invention will be described in further detail with reference to Examples. However, it should be understood that the present invention is by no means restricted to such specific Examples.

Example 1

| | |
|---|---|
| (1) Nicosulfuron (purity 93.4%) | 88.2 parts by weight |
| (2) Sodium dialkylnaphthalene sulfonate (tradename: Supragil WP, manufactured by Rhodia, Nicca, Ltd.) | 1.0 part by weight |
| (3) Sodium polycarboxylate (tradename: Geropon T/36 manufactured by Rhodia Nicca, Ltd.) | 1.0 part by weight |
| (4) White carbon (tradename, CARPLEX #80, manufactured by DSL. Japan Co., Ltd.) | 3.0 parts by weight |
| (5) Clay (tradename: ST kaolin, manufactured by TAKEHARA KAGAKU KOGYO CO., LTD.) | 6.8 parts by weight |

The above components were mixed to obtain a wettable powder. The wettable powder is diluted with water together with dipolyoxyethylene alkyl ether phosphate (tradename:

NIKKOL DDP-8, manufactured by NIKKO CHEMICALS CO., LTD.), followed by applying.

Example 2

A wettable powder prepared in accordance with the above Example 1 is diluted with water together with NIKKOL DDP-8 (tradename) and disodium hydrogenphosphate, followed by applying.

Example 3

(I)

| | | |
|---|---|---|
| (1) | Sodium dodecylbenzenesulfonate (tradename: Sorpol 5060, manufactured by TOHO Chemical Industry Co., Ltd.) | 2.0 parts by weight |
| (2) | Polyoxyethylene nonylphenyl ether sulfate (tradename: Sorpol 5073, manufactured by TOHO Chemical Industry Co., Ltd.) | 3.0 parts by weight |
| (3) | Polyoxyethylene dodecylphenyl ether (tradename: NOIGEN EA-33, manufactured by DAI-ICHI KOGYO SEIYAKU CO., LTD.) | 1.0 part by weight |
| (4) | Clay (tradename: OQ clay, manufactured by NIHON TAIKA GENRYO Co., Ltd.) | 78.0 parts by weight |
| (5) | White carbon (tradename: CARPLEX CS-7, manufactured by DSL. Japan Co., Ltd.) | 16.0 parts by weight |

The above components are mixed to obtain a composition (A).

(II)

| | | |
|---|---|---|
| (1) | Foramsulfuron (purity at least 98%) | 10.0 parts by weight |
| (2) | The above composition (A) | 90.0 parts by weight |

The above components were mixed to obtain a wettable powder. The wettable powder is diluted with water together with NIKKOL DDP-8 (tradename), followed by applying.

Example 4

A wettable powder prepared in accordance with the above Example 3 is diluted with water together with NIKKOL DDP-8 (tradename) and disodium hydrogenphosphate, followed by applying.

Example 5

| | | |
|---|---|---|
| (1) | Iodosulfuron (purity at least 98%) | 10.0 parts by weight |
| (2) | The above composition (A) | 90.0 parts by weight |

The above components are mixed to obtain a wettable is powder, which is diluted with water together with tripolyoxyethylene alkyl ether phosphate (tradename: NIKKOL TDP-8, manufactured by NIKKO CHEMICALS CO., LTD.), followed by applying.

Example 6

A wettable powder prepared in accordance with the above Example 5 is diluted with water together with NIKKOL TDP-8 (tradename) and disodium hydrogenphosphate, followed by applying.

Test Example 1

Upland field soil was put into a 1/1,000,000 ha pot, and seeds of crabgrass (*Digitaria sanguinalis* L.) were sown and grown in a greenhouse. When crabgrass reached 4.0 to 4.3 leaf stage, a prescribed amount (25 g a.i./ha) of a wettable powder comprising nicosulfuron as an active ingredient prepared in accordance with the above Example 1 was diluted with water in an amount of 300 L/ha, and a surfactant (tradename: NIKKOL DLP-10, NIKKOL DDP-8, NIKKOL DDP-10 or NIKKOL TDP-8, manufactured by NIKKO CHEMICALS CO., LTD.) containing a POA alkyl ether phosphate was added thereto at a concentration of 0.05 wt %, followed by foliar application. Further, for comparison, foliar application was carried out in the same manner by using an alkylaryl polyglycol ether type surfactant (tradename: Citowett, manufactured by BASF France) (at a concentration of 0.3 wt %) instead of the above surfactant.

The state of growth of crabgrass was assessed visually 21 days after application, to determine the growth inhibition rate (%) 0% (the same as the untreated plot) to 100% (complete kill), and the results are shown in Table 1.

TABLE 1

| | Surfactant (tradename) | Added concentration (%) | Growth inhibition rate (%) |
|---|---|---|---|
| The present invention | NIKKOL DLP-10 | 0.05 | 84 |
| | NIKKOL DDP-8 | 0.05 | 88 |
| | NIKKOL DDP-10 | 0.05 | 87 |
| | NIKKOL TDP-8 | 0.05 | 78 |
| Comparison | Citowett | 0.3 | 23 |

Test Example 2

Upland field soil was put into a 1/1,000,000 ha pot, and seeds of common cocklebur (*Xanthium strumarium* L.) were sown and grown in a greenhouse. When common cocklebur reached 2.1 to 2.2 leaf stage, a prescribed amount (25 g a.i./ha) of a wettable powder comprising nicosulfuron as an active ingredient prepared in accordance with the above Example 1 was diluted with water in an amount of 300 L/ha, and a surfactant (tradename: NIKKOL DLP-10, NIKKOL DDP-8, NIKKOL DDP-10, NIKKOL TDP-8 or NIKKOL TDP-10, manufactured by NIKKO CHEMICALS CO., LTD.) containing a POA alkyl ether phosphate was added thereto at a concentration of 0.05 wt %, followed by foliar application. Further, for comparison, foliar application was carried out in the same manner by using an ethoxylated fatty amine type surfactant (tradename: Lutensol FA-15T, manufactured by BASF) instead of the above surfactant.

The state of growth of common cocklebur was evaluated 21 days after application in the same manner as in Test Example 1, and the results are shown in Table 2.

TABLE 2

| | Surfactant (tradename) | Added concentration (%) | Growth inhibition rate (%) |
|---|---|---|---|
| The present invention | NIKKOL DLP-10 | 0.05 | 83 |
| | NIKKOL DDP-8 | 0.05 | 77 |
| | NIKKOL DDP-10 | 0.05 | 87 |

TABLE 2-continued

|  | Surfactant (tradename) | Added concentration (%) | Growth inhibition rate (%) |
|---|---|---|---|
|  | NIKKOL TDP-8 | 0.05 | 87 |
|  | NIKKOL TDP-10 | 0.05 | 87 |
| Comparison | Lutensol FA-15T | 0.05 | 60 |

Test Example 3

Upland field soil was put into a 1/1,000,000 ha pot, and seeds of crabgrass (*Digitaria sanguinalis* L.) were sown and grown in a greenhouse. When crabgrass, reached 4.0 to 4.3 leaf stage, a prescribed amount (25 g a.i./ha) of a wettable powder comprising nicosulfuron as an active ingredient prepared in accordance with the above Example 1 was diluted with water in an amount of 300 L/ha, and a surfactant (tradename: NIKKOL DLP-10, NIKKOL DDP-8 or NIKKOL TDP-2, manufactured by NIKKO CHEMICALS CO., LTD.) containing a POA alkyl ether phosphate was added thereto at a concentration of 0.025 wt % or 0.05 wt %, and a salt (disodium hydrogenphosphate) was further added thereto at a concentration of 0.005 wt %, followed by foliar application. Further, for comparison, foliar application was carried out in the same manner by using Citowett (tradename) (at a concentration of 0.3 wt %) instead of the above surfactant.

The state of growth of crabgrass was evaluated 21 days after application in the same manner as in Test Example 1. The results are shown in Table 3.

TABLE 3

|  | Surfactant (tradename) | Added concentration of surfactant (%) | Added concentration of salt (%) | Growth inhibition rate (%) |
|---|---|---|---|---|
| The present invention | NIKKOL DLP-10 | 0.025 | 0.005 | 72 |
|  | NIKKOL DDP-8 | 0.025 | 0.005 | 80 |
|  | NIKKOL TDP-2 | 0.05 | 0.005 | 83 |
| Comparison | Citowett | 0.3 | — | 23 |

Test Example 4

Upland field soil was put into a 1/1,000,000 ha pot, and seeds of crabgrass (*Digitaria sanguinalis* L.) were sown and grown in a greenhouse. When crabgrass reached 4.2 to 4.4 leaf stage, a prescribed amount (30 g a.i./ha) of a wettable powder comprising foramsulfuron as an active ingredient prepared in accordance with the above Example 3 was diluted with water in an amount of 300 L/ha, and a surfactant (tradename: NIKKOL DDP-8, manufactured by NIKKO CHEMICALS CO., LTD.) containing a POA alkyl ether phosphate was added thereto at a concentration of 0.025 wt %, or a salt (disodium hydrogenphosphate) was further added thereto at a concentration of 0.005 wt %, followed by foliar application. Further, for comparison, foliar application was carried out in the same manner by using Citowett (tradename) (at a concentration of 0.2 wt %) instead of the above surfactant.

The state of growth of crabgrass was evaluated 20 days after application in the same manner as in Test Example 1. The results are shown in Table 4.

TABLE 4

|  | Surfactant (tradename) | Added concentration of surfactant (%) | Added concentration of salt (%) | Growth inhibition rate (%) |
|---|---|---|---|---|
| The present invention | NIKKOL DDP-8 | 0.025 | — | 83 |
|  | NIKKOL DDP-8 | 0.025 | 0.005 | 89 |
| Comparison | Citowett | 0.2 | — | 23 |

Test Example 5

Upland field soil was put into a 1/1,000,000 ha pot, and seeds of crabgrass (*Digitaria sanguinalis* L.) were sown and grown in a greenhouse. When crabgrass reached 4.0 to 4.3 leaf stage, a prescribed amount (25 g a.i./ha) of a wettable powder comprising flazasulfuron as an active ingredient (tradename: SHIBAGEN, manufactured by ISHIHARA SANGYO KAISHA, LTD.) was diluted with water in an amount of 300 L/ha, and a surfactant (tradename: NIKKOL DDP-8, manufactured by NIKKO CHEMICALS CO., LTD.) containing a POA alkyl ether phosphate was added thereto at a concentration of 0.025 wt %, or a salt (disodium hydrogenphosphate) was further added thereto at a concentration of 0.005 wt %, followed by foliar application. Further, for comparison, foliar application was carried out in the same manner by using Citowett (tradename) (at a concentration of 0.2 wt %) instead of the above surfactant.

The state of growth of crabgrass was evaluated 20 days after application in the same manner as in Test Example 1. The results are shown in Table 5.

TABLE 5

|  | Surfactant (tradename) | Added concentration of surfactant (%) | Added concentration of salt (%) | Growth inhibition rate (%) |
|---|---|---|---|---|
| The present invention | NIKKOL DDP-8 | 0.025 | — | 83 |
|  | NIKKOL DDP-8 | 0.025 | 0.005 | 94 |
| Comparison | Citowett | 0.2 | — | 70 |

Test Example 6

Upland field soil was put into a 1/1,000,000 ha pot, and seeds of crabgrass (*Digitaria sanguinalis* L.) were sown and grown in a greenhouse. When crabgrass reached 4.3 to 4.5 leaf stage, a prescribed amount (5 g a.i./ha) of water-dispersible granules (tradename: Titus, manufactured by DuPont) comprising rimsulfuron as an active ingredient were diluted with water in an amount of 300 L/ha, and a surfactant (tradename: NIKKOL DDP-8, manufactured by NIKKO CHEMICALS CO., LTD., or tradename: ADEKA COL PS-440E, manufactured by ADEKA CORPORATION) containing a POA alkyl ether phosphate was added thereto at a concentration of 0.025 wt %, followed by foliar application. Further, for comparison, foliar application was carried out in the same manner by using Citowett (tradename) or polyoxyethylene alkyl ether (tradename: MonFast, manufactured by Monsanto) (at a concentration of 0.2 wt %) instead of the above surfactant.

The state of growth of crabgrass was evaluated 21 days after application in the same manner as in Test Example 1, and the results are shown in Table 6.

TABLE 6

| | Surfactant (tradename) | Added concentration (%) | Growth inhibition rate (%) |
|---|---|---|---|
| The present invention | NIKKOL DDP-8 | 0.025 | 70 |
| | ADEKA COL PS-440E | 0.025 | 74 |
| Comparison | Citowett | 0.2 | 58 |
| | MonFast | 0.2 | 55 |

Example 7

Upland field soil was put into a 1/1,000,000 ha pot, and seeds of barnyardgrass (*Echinochloa crus-galli* L.) were sown and grown in a greenhouse. When barnyardgrass reached 5.0 to 5.2 leaf stage, a prescribed amount (7.5 g a.i./ha) of water-dispersible granules (tradename: Hussar, manufactured by Bayer) comprising iodosulfuron-methyl-sodium as an active ingredient were diluted with water in an amount of 300 L/ha, and NIKKOL DDP-8 (tradename) or ADEKA COL PS-440E (tradename) was added thereto at a concentration of 0.025 wt %, followed by foliar application. Further, for comparison, foliar application was carried out in the same manner by using Citowett (tradename) (at a concentration of 0.2 wt %) instead of the above surfactant.

The state of growth of barnyardgrass was evaluated 21 days after application in the same manner as in Test Example 1, and the results are shown in Table 7.

TABLE 7

| | Surfactant (tradename) | Added concentration (%) | Growth inhibition rate (%) |
|---|---|---|---|
| The present invention | NIKKOL DDP-8 | 0.025 | 78 |
| | ADEKA COL PS-440E | 0.025 | 75 |
| Comparison | Citowett | 0.2 | 60 |

Test Example 8

Upland field soil was put into a 1/1,000,000 ha pot, and seeds of velvetleaf (*Abutilon theophrasti* MEDIC.) were sown and grown in a greenhouse. When velvetleaf reached 3.5 to 4.0 leaf stage, a prescribed amount (20 g a.i./ha) of a wettable powder (tradename: "Shado", manufactured by Nissan Chemical Industries, Ltd.) comprising halosulfuron-methyl as an active ingredient was diluted with water in an amount of 300 L/ha, and NIKKOL DDP-8 (tradename) or ADEKA COL PS-440E (tradename) was added thereto at a concentration of 0.05 wt %, followed by foliar application. Further, for comparison, foliar application was carried out in the same manner by using Citowett (tradename) or MonFast (tradename) (at a concentration of 0.1 wt %) instead of the above surfactant.

The state of growth of velvetleaf was evaluated 22 days after application in the same manner as in Test Example 1, and the results are shown in Table 8.

TABLE 8

| | Surfactant (tradename) | Added concentration (%) | Growth inhibition rate (%) |
|---|---|---|---|
| The present invention | NIKKOL DDP-8 | 0.05 | 87 |
| | ADEKA COL PS-440E | 0.05 | 91 |
| Comparison | Citowett | 0.1 | 80 |
| | MonFast | 0.1 | 79 |

Test Example 9

Upland field soil was put into a 1/1,000,000 ha pot, and seeds of crabgrass (*Digitaria sanguinalis* L.) were sown and grown in a greenhouse. When crabgrass reached 4.0 to 4.2 leaf stage, a prescribed amount (15 g a.i./ha) of water-dispersible granules (tradename: Monument, manufactured by Syngenta) comprising trifloxysulfuron-sodium as an active ingredient were diluted with water in an amount of 300 L/ha, and NIKKOL DDP-8 (tradename) was added thereto at a concentration of 0.025 wt %, or a salt (disodium hydrogenphosphate) was further added thereto at a concentration of 0.005 wt %, followed by foliar application. Further, for comparison, foliar application was carried out in the same manner by using Citowett (tradename) (at a concentration of 0.2 wt %) instead of the above surfactant.

The state of growth of crabgrass was evaluated 20 days after application in the same manner as in Test Example 1, and the results are shown in Table 9.

TABLE 9

| | Surfactant (tradename) | Added concentration of surfactant (%) | Added concentration of salt (%) | Growth inhibition rate (%) |
|---|---|---|---|---|
| The present invention | NIKKOL DDP-8 | 0.025 | — | 83 |
| | NIKKOL DDP-8 | 0.025 | 0.005 | 89 |
| Comparison | Citowett | 0.2 | — | 68 |

Test Example 10

Upland field soil was put into a 1/1,000,000 ha pot, and seeds of black nightshade (*Solanum nigrum* L.) were sown and grown in a greenhouse. When black nightshade reached 3.4 to 3.8 leaf stage, a prescribed amount (40 g a.i./ha) of water-dispersible granules (tradename: Biathlon, manufactured by BASF) comprising tritosulfuron as an active ingredient were diluted with water in an amount of 300 L/ha, and NIKKOL DDP-8 (tradename) or ADEKA COL PS-440E (tradename) was added thereto at a concentration of 0.05 wt %, or a salt (disodium hydrogenphosphate) was further added thereto at a concentration of 0.005 wt %, followed by foliar application. Further, for comparison, foliar application was carried out in the same manner by using Citowett (tradename) or MonFast (tradename) (at a concentration of 0.1 wt %) instead of the above surfactant.

The state of growth of black nightshade was evaluated 22 days after application in the same manner as in Test Example 1, and the results are shown in Table 10.

TABLE 10

| | Surfactant (tradename) | Added concentration of surfactant (%) | Added concentration of salt (%) | Growth inhibition rate (%) |
|---|---|---|---|---|
| The present invention | NIKKOL DDP-8 | 0.05 | — | 92 |
| | NIKKOL DDP-8 | 0.05 | 0.005 | 94 |
| | ADEKA COL PS-440E | 0.05 | — | 90 |
| | ADEKA COL PS-440E | 0.05 | 0.005 | 96 |
| Comparison | MonFast | 0.1 | — | 77 |
| | Citowett | 0.1 | — | 80 |

Test Example 11

Upland field soil was put into a 1/1,000,000 ha pot, and seeds of velvetleaf (*Abutilon theophrasti* MEDIC.) were sown and grown in a greenhouse. When velvetleaf reached 3.5 to 4.0 leaf stage, a prescribed amount (40 g a.i./ha) of water-dispersible granules (tradename: Biathlon, manufactured by BASF) comprising tritosulfuron as an active ingredient were diluted with water in an amount of 300 L/ha, and NIKKOL DDP-8 (tradename) or ADEKA COL PS-440E (tradename) was added thereto at a concentration of 0.05 wt %, or a salt (disodium hydrogenphosphate) was further added thereto at a concentration of 0.005 wt %, followed by foliar application. Further, for comparison, foliar application was carried out in the same manner by using MonFast (tradename) (at a concentration of 0.1 wt %) instead of the above surfactant.

The state of growth of velvetleaf was evaluated 22 days after application in the same manner as in Test Example 1, and the results are shown in Table 11.

TABLE 11

| | Surfactant (tradename) | Added concentration of surfactant (%) | Added concentration of salt (%) | Growth inhibition rate (%) |
|---|---|---|---|---|
| The present invention | ADEKA COL PS-440E | 0.05 | — | 75 |
| | ADEKA COL PS-440E | 0.05 | 0.005 | 82 |
| Comparison | MonFast | 0.1 | — | 53 |

Test Example 12

Upland field soil was put into a 1/1,000,000 ha pot, and seeds of velvetleaf (*Abutilon theophrasti* MEDIC.) were sown and grown in a greenhouse. When velvetleaf reached 3.5 to 4.0 leaf stage, a prescribed amount (20 g a.i./ha) of a wettable powder comprising prosulfuron as an active ingredient prepared in accordance with the above Example 3 was diluted with water in an amount of 300 L/ha, and NIKKOL DDP-8 (tradename) was added thereto at a concentration of 0.05 wt %, or a salt (disodium hydrogenphosphate) was further added thereto at a concentration of 0.005 wt %, followed by foliar application. Further, for comparison, foliar application was carried out in the same manner by using Citowett (tradename) or MonFast (tradename) (at a concentration of 0.1 wt %) instead of the above surfactant.

The state of growth of velvetleaf was evaluated 22 days after application in the same manner as in Test Example 1, and the results are shown in Table 12.

TABLE 12

| | Surfactant (tradename) | Added concentration of surfactant (%) | Added concentration of salt (%) | Growth inhibition rate (%) |
|---|---|---|---|---|
| The present invention | NIKKOL DDP-8 | 0.05 | — | 76 |
| | NIKKOL DDP-8 | 0.05 | 0.005 | 90 |
| Comparison | MonFast | 0.1 | — | 50 |
| | Citowett | 0.1 | — | 30 |

Test Example 13

Upland field soil was put into a 1/1,000,000 ha pot, and seeds of crabgrass (*Digitaria sanguinalis* L.) were sown and grown in a greenhouse. When crabgrass reached 4.2 to 4.5 leaf stage, a prescribed amount (20 g a.i./ha) of a wettable powder comprising nicosulfuron as an active ingredient prepared in accordance with the above Example is 1 was diluted with water in an amount of 300 L/ha, and NIKKOL DDP-8 (tradename) was added thereto at a concentration of 0.025 wt %, and a salt (disodium hydrogenphosphate, trisodium citrate dihydrate, sodium succinate hexahydrate, disodium EDTA hexahydrate, or sodium glutamate) was further added thereto at a concentration of 0.005 wt % (based on anhydride), followed by foliar application.

The state of growth of crabgrass was evaluated 21 days after application in the same manner as in Test Example 1, and the results are shown in Table 13.

TABLE 13

| | Surfactant (tradename) | Added concentration of surfactant (%) | Salt | Added concentration of salt (%) (based on anhydride) | Growth inhibition rate (%) |
|---|---|---|---|---|---|
| The present invention | NIKKOL DDP-8 | 0.025 | — | 0 | 53 |
| | | 0.025 | Disodium hydrogen-phosphate | 0.005 | 83 |
| | | 0.025 | Trisodium citrate | 0.005 | 78 |
| | | 0.025 | Sodium succinate | 0.005 | 63 |
| | | 0.025 | Disodium EDTA | 0.005 | 82 |
| | | 0.025 | Sodium glutamate | 0.005 | 73 |

The entire disclosure of Japanese Patent Application No. 2006-083322 filed on Mar. 24, 2006 including specification, claims and summary is incorporated herein by reference in its entirety.

The invention claimed is:

1. A herbicidal composition comprising (1) a herbicidal sulfonylurea compound or its salt and (2) a polyoxyalkylene alkyl ether phosphate or its salt, wherein (1) the herbicidal sulfonylurea compound or its salt is at least one member selected from the group consisting of flazasulfuron, foramsulfuron, halosulfuron-methyl, iodosulfuron-methyl-sodium, nicosulfuron, prosulfuron, rimsulfuron, trifloxysulfuron-sodium and tritosulfuron, wherein the alkyl moiety in the POA alkyl ether phosphate has from about 8 to about 20 carbon atoms, and wherein the number of addition of POA moiety in the POA alkyl ether phosphate is from about 1 to about 20.

2. The herbicidal composition according to claim 1, which further contains (3) a salt.

3. The herbicidal composition according to claim 1, wherein (1) the herbicidal sulfonylurea compound or its salt is at least one member selected from the group consisting of flazasulfuron, foramsulfuron and nicosulfuron.

4. The herbicidal composition according to claim 2, wherein (3) the salt is an inorganic salt.

5. The herbicidal composition according to claim 4, wherein the inorganic salt is a phosphate.

6. The herbicidal composition according to claim 5, wherein the phosphate is a sodium salt.

7. A method for controlling undesired plants or inhibiting their growth, which comprises applying (1) a herbicidal sulfonylurea compound or its salt and (2) a polyoxyalkylene alkyl ether phosphate or its salt, to the undesired plants or to a place where they grow, wherein (1) the herbicidal sulfonylurea compound or its salt is at least one member selected from the group consisting of flazasulfuron, foramsulfuron, halosulfuron-methyl, iodosulfuron-methyl-sodium, nicosulfuron, prosulfuron, rimsulfuron, trifloxysulfuron-sodium and tritosulfuron, wherein the alkyl moiety in the POA alkyl ether phosphate has from about 8 to about 20 carbon atoms, and wherein the number of addition of POA moiety in the POA alkyl ether phosphate is from about 1 to about 20.

8. The method according to claim 7, wherein (3) a salt is further applied.

9. A method for controlling undesired plants or inhibiting their growth, which comprises diluting (1) a herbicidal sulfonylurea compound or its salt with water in an amount of from 30 to 5,000 L/ha, together with (2) a polyoxyalkylene alkyl ether phosphate or its salt, and applying the diluted liquid to the undesired plants or to a place where they grow, wherein (1) the herbicidal sulfonylurea compound or its salt is at least one member selected from the group consisting of flazasulfuron, foramsulfuron, halosulfuron-methyl, iodosulfuron-methyl-sodium, nicosulfuron, prosulfuron, rimsulfuron, trifloxysulfuron-sodium and tritosulfuron, wherein the alkyl moiety in the POA alkyl ether phosphate has from about 8 to about 20 carbon atoms, and wherein the number of addition of POA moiety in the POA alkyl ether phosphate is from about 1 to about 20.

10. The method according to claim 9, wherein (3) a salt is further applied.

11. The method according to claim 9, wherein (2) the polyoxyalkylene alkyl ether phosphate or its salt is, used in an amount of from 0.005 to 4 wt % based on the diluted liquid.

12. The method according to claim 10, wherein (2) the polyoxyalkylene alkyl ether phosphate or its salt is used in an amount of from 0.005 to 4 wt % based on the diluted liquid, and (3) the salt is used in an amount of from 0.0001 to 0.05 wt % based on the diluted liquid.

13. A method for improving the herbicidal effect of (1) a herbicidal sulfonylurea compound or its salt, comprising mixing (2) a polyoxyalkylene alkyl ether phosphate or its salt with the herbicidal sulfonylurea compound or its salt, wherein (1) the herbicidal sulfonylurea compound or its salt is at least one member selected from the group consisting of flazasulfuron, foramsulfuron, halosulfuron-methyl, iodosulfuron-methyl-sodium, nicosulfuron, prosulfuron, rimsulfuron, trifloxysulfuron-sodium and tritosulfuron, wherein the alkyl moiety in the POA alkyl ether phosphate has from about 8 to about 20 carbon atoms, and wherein the number of addition of POA moiety in the POA alkyl ether phosphate is from about 1 to about 20.

14. The method according to claim 13, wherein (3) a salt is further mixed.

* * * * *